(12) United States Patent
Boutchich et al.

(10) Patent No.: US 8,405,041 B2
(45) Date of Patent: Mar. 26, 2013

(54) ELECTRODE FOR AN IONIZATION CHAMBER AND METHOD PRODUCING THE SAME

(75) Inventors: Mohamed Boutchich, Heverlee (BE); Vijayaraghavan Madakasira, Louvain (BE); Nader Akil, Sterrebeek (BE)

(73) Assignee: NXP B.V., Eindhoven (NL)

( * ) Notice: Subject to any disclaimer, the term of this patent is extended or adjusted under 35 U.S.C. 154(b) by 121 days.

(21) Appl. No.: 12/743,288

(22) PCT Filed: Nov. 17, 2008

(86) PCT No.: PCT/IB2008/054796
§ 371 (c)(1),
(2), (4) Date: May 17, 2010

(87) PCT Pub. No.: WO2009/066220
PCT Pub. Date: May 28, 2009

(65) Prior Publication Data
US 2010/0253359 A1    Oct. 7, 2010

(30) Foreign Application Priority Data
Nov. 20, 2007  (EP) .................................. 07121110

(51) Int. Cl.
*H01L 21/302* (2006.01)
(52) U.S. Cl. ............... 250/382; 250/374; 250/336.1; 977/762; 977/953
(58) Field of Classification Search .............. 250/382, 250/374, 336.1; 977/762, 953
See application file for complete search history.

(56) References Cited

U.S. PATENT DOCUMENTS

| | | | | |
|---|---|---|---|---|
| 5,911,863 | A * | 6/1999 | Vetter et al. ............... | 205/103 |
| 6,297,063 | B1 * | 10/2001 | Brown et al. ............... | 438/2 |
| 6,340,822 | B1 * | 1/2002 | Brown et al. ............... | 257/25 |
| 6,401,526 | B1 * | 6/2002 | Dai et al. ................. | 73/105 |
| 6,448,777 | B1 * | 9/2002 | Abdel-Rahman et al. .... | 324/464 |
| 6,531,877 | B1 * | 3/2003 | Abdel-Rahman ........... | 324/464 |
| 6,864,162 | B2 * | 3/2005 | Jin ......................... | 438/551 |
| 6,984,579 | B2 * | 1/2006 | Nguyen et al. ............. | 438/622 |
| 7,163,659 | B2 | 1/2007 | Stasiak et al. | |
| 7,168,484 | B2 * | 1/2007 | Zhang et al. ............... | 165/185 |
| 7,186,986 | B2 * | 3/2007 | Hinderer et al. ........... | 250/375 |
| 7,476,852 | B2 * | 1/2009 | Bonne et al. .............. | 250/288 |
| 2001/0023986 | A1 * | 9/2001 | Mancevski ................ | 257/741 |
| 2003/0034781 | A1 * | 2/2003 | Abdel-Rahman ........... | 324/464 |

(Continued)

FOREIGN PATENT DOCUMENTS
EP    1 426 756 A1    6/2004
EP    1 736 760 A2    12/2006

(Continued)

OTHER PUBLICATIONS
Modi, et al., "Carbon Nanotube Electrode Films for Gas Sensing", American Institute of Aeronautics and Astronautics, Inc., pp. 441-450 (2004).

(Continued)

*Primary Examiner* — David Porta
*Assistant Examiner* — Djura Malevic

(57) ABSTRACT

An electrode for an ionization chamber and an ionization chamber including an electrode are provided wherein the electrode comprises a substrate comprising a first material, and a plurality of nanowires extending from the substrate and manufactured by processing the first material of the substrate.

20 Claims, 6 Drawing Sheets

U.S. PATENT DOCUMENTS

| | | |
|---|---|---|
| 2003/0111336 A1 | 6/2003 | Lee et al. |
| 2003/0165418 A1* | 9/2003 | Ajayan et al. ............. 423/447.2 |
| 2005/0009224 A1* | 1/2005 | Yang et al. ...................... 438/57 |
| 2005/0233585 A1* | 10/2005 | Lai et al. ...................... 438/678 |
| 2005/0269286 A1 | 12/2005 | Sharma et al. |
| 2006/0006463 A1* | 1/2006 | Islam et al. .................. 257/347 |
| 2006/0068195 A1* | 3/2006 | Majumdar et al. ............ 428/323 |
| 2006/0134392 A1* | 6/2006 | Hantschel et al. ............ 428/210 |
| 2009/0321633 A1* | 12/2009 | Blick et al. .................... 250/307 |

FOREIGN PATENT DOCUMENTS

| | | |
|---|---|---|
| GB | 2 413 890 A | 11/2005 |
| JP | 2005-351646 A | 12/2005 |
| WO | 03/083919 A2 | 10/2003 |

OTHER PUBLICATIONS

Hui, et al, "A Novel Gas-Ionization Sensor Based on Aligned Multi-Walled Carbon Nanotubes", Inst. of Physics Publishing, Measurement Science & Technology 17, pp. 2799-2805 (2006).

Longwitz, et al., "Study of Gas Ionization Schemes for Micro Devices", 11th Int'l. Conf. on Solid-State Sensors and Actuators, Munich, Germany, 4 pgs. (Jun. 2001).

International Search Report for Int'l. Patent Appln. No. PCT/IB2008/054796 (Mar. 31, 2009).

Written Opinion for Int'l. Patent Appln. No. PCT/IB2008/054796.

\* cited by examiner

ELECTRODE FOR AN IONIZATION CHAMBER AND METHOD PRODUCING THE SAME

FIELD OF THE INVENTION

The invention relates to an electrode for an ionization chamber.

The invention further relates an ionization chamber, in particular it relates to an ionization detector.

Moreover, the invention relates to a method of producing an electrode for an ionization chamber.

BACKGROUND OF THE INVENTION

Although gas chromatograph mass spectrometer (GCMS) is a robust and reliable technique to monitor and determine constituents of a gas sample, the significant size and cost has appealed for inexpensive and smaller detection methods. Nowadays, sensor manufacturers are producing instruments that have more advanced detection capabilities and cover a wider range of advanced applications by using micromachined technology. While continuing to use mature technologies, vehicle manufacturers for example are increasing the sophistication of the electronic systems used in their products. Many manufacturers clamor for chemical sensors to provide real-time analysis of, for example, exhaust fumes and determine the concentration of hydrocarbons in fuel vapors recovery systems.

In general, gas sensors operate by a variety of fundamentally different mechanisms. Ionization sensors work by fingerprinting the ionization characteristics of distinct gases, but they are limited by their huge bulky architecture.

SUMMARY OF THE INVENTION

Thus, there may be a need to provide an improved electrode for an ionization chamber, an ionization chamber and a method producing an electrode for an ionization chamber, wherein the ionization chamber may have a smaller size, and may be operated at a small voltage.

In order to meet the need defined above, an electrode for an ionization chamber, an ionization chamber, and a method of producing an electrode for an ionization chamber according to the independent claims are provided.

According to an exemplary embodiment an electrode for an ionization chamber is provided wherein the electrode comprises a substrate comprising a first material, and a plurality of nanowires extending from the substrate and manufactured by processing the first material of the substrate.

According to an exemplary embodiment an ionization chamber is provided wherein the ionization chamber comprises an electrode according to an exemplary embodiment of the invention a cavity, and an further electrode, wherein a tip region of at least some or all of the plurality of nanowires extend into the cavity, and wherein the further electrode is arranged in such a way that the tip region and the electrode are facing each other. In particular, the cavity may be enclosed at least on one side by the further electrode, e.g. the further electrode may form a wand of the cavity, and the further electrode and the tip region, e.g. a region of the nanowires not covered by a dielectric layer, may face each other but may be not in direct contact, i.e. may be separated from each other.

According to an exemplary embodiment of the invention a method of manufacturing an electrode is provided, wherein the method comprises providing a substrate, and patterning the substrate in such a way that a plurality of nanowires are generated which extend from the substrate by processing the substrate.

In this application, the term "ionization chamber" may particularly denote any device or housing which is adapted to ionize a fluid, e.g. a gas or fluid, and/or to detect such an ionized fluid, e.g. an ionization detector. Such an ionization chamber may in particular be adapted to be coupled to and/or may comprise a voltage or energy source, e.g. a battery.

In this application, the term "nanowires" may particularly denote any small structure comprising or made of electrically conductive material. In particular, an extension or size of the nanowire in a first or longitudinal direction may be larger than in the directions perpendicular to that longitudinal direction, so that a wire like structure is formed. Moreover, the size of the whole nanowire is in the low micrometer or submicrometer range. For example, the extension in the longitudinal direction may be between a couple of micrometers, e.g. about 20 µm, and several nanometers, e.g. 50 nm, while the diameter of the nanowire may be in the range of about 2 nm to about 200 nm. In particular, a nanowire may have a length of between about 100 nm and about 10 µm and may have a diameter of between about 5 nm and about 100 nm. More particularly, the nanowire may have a length between about 250 nm and about 1 µm and a diameter between about 10 nm and about 50 nm.

An electrode according to an exemplary embodiment may provide a small sized electrode which may be manufactured by using known silicon technology contrary to electrodes which employ grown nanowires or nanotubes, e.g. carbon nanotubes. In particular, the use of the known silicon technology may reduce the costs and/or may increase the yield of the manufacturing process. In particular, it may be much easier to manufacture an array of nanowires having a predetermined or fixed relation or arrangement with respect to each other, when using the silicon technology, e.g. CMOS technology, as it would be when firstly growing carbon nanotubes which are then fixed to a substrate. Thus, it may be possible to provide micro/nanometer-scale devices that can be fabricated as discrete devices or large arrays, using the technology of integrated circuit manufacturing. Thus, simpler, standardized integrated chip component technology may be used. In particular, such micro/nanometer-scale devices may exhibit lower power consumption and may not need risky high-voltage operation as known heavy bulky devices. Moreover, a low operation voltage that may be compatible with CMOS devices may provide rapid response time together with a package size of the device of a few $mm^3$, for example. Such miniature detectors or sensors may be designed and fabricated by integrating the sensors onto the same semiconductor substrate, e.g. form the nanowires from the substrate by processing the same, as the electronic circuitry. Consequently, the signal to noise ration may be enhanced as well as the sensitivity. Since standard batch processing, as in the IC industry, may be applicable to manufacturing electrodes of devices and the devices itself, a huge number of identical sensors may be producible in one run, thus possibly improving their performance/cost ratio. Furthermore, the miniaturization of sensors may not only contribute to their potentially low cost, but may also allow them to be integrated with microelectronic circuits, thus, possibly further enhancing their performance.

Furthermore, it may even be possible to integrate the manufacturing process of the electrode into the manufacturing process of the whole micro/nanometer-scale devices, e.g. a micro/nanometer-scale ionization chamber or ionization detector so that no special component has to be integrated. In particular, the manufacturing process of the electrode may be a CMOS compatible integration scheme.

Thus, a gist of an exemplary aspect of the invention may be seen in the fact that an electrode for a sensor and/or ionization chamber may be provided having a plurality of nanowires, which are formed by processing a semiconductor substrate. Such a processing may be done by well known structuring, e.g. by using known etching processes. Such etching processes may in particular lead to a well defined arrangement of the plurality of nanowires on the substrate, possibly leading to an improved performance of the sensor. In particular, a vertically aligned nanostructure array covering an electrode, e.g. a cathode, may be produced, which may be more compatible to produce a consistent nanometer-scale surface topology than conventional planar electrodes.

Next, further exemplary embodiments of the invention will be described.

In the following, further exemplary embodiments of the electrode for an ionization chamber will be explained. However, these embodiments also apply for the ionization chamber and the method of producing an electrode.

According to another exemplary embodiment of the electrode the plurality of nanowires is manufactured by etching. Etching may be an efficient way to manufacture the nanowires out of the substrate, since etching procedures well known in the semiconductor technology may be used so that a high reproducibility of the nanowires and high accuracy of the achieved arrangement may be possible, Furthermore, the etching processes may be fully integrated into standard processes.

According to another exemplary embodiment of the electrode at least some of the plurality of nanowires comprises a tip region. In particular, the tip region may be formed by a conical tip region, e.g. may be formed by a sharp tip. The provision of such tips in particular of sharp tips, may be a suitable measure to generate very high electric fields in case the tips are spaced from each other in such a way that no shielding or superimposing of the electric fields of the single tips occur. Such very high electric field may decrease the breakdown voltage so that a detector comprising such an electrode may exhibit an increased sensitivity and/or an increase performance when ionizing fluids. Thus, it may be possible to manufacture compact, possibly battery-powered and safe operation of such detectors. A sharp tip may in particular be characterized in that an opening angle of a sharp tip may be below 45°, preferably it may be below 30°. For instance, the opening angle may be between 10° and 25° or even below, e.g. between 5° and 10°.

According to another exemplary embodiment of the electrode the first material is a semiconductor material. In particular, the base member may be a semiconductor substrate, e.g. a silicon substrate or a substrate comprising germanium as a material.

According to another exemplary embodiment of the electrode at least some of the plurality of nanowires are at least partially silicided. In particular parts of the nanowires may be silicided or metallized by using any suitable silicide phase, e.g. by using $TiSi_2$ NiSi, or $CoSi_2$, Moreover, some or all nanowires may be silicided partly of fully. For example, only a tip region of the nanowires may be silicided, e.g. a tip region that is not covered by a dielectric material or dielectric layer.

The silicide may increase the lifetime of the nanowire and/or may further increase an electric field in the region of the tips of the nanowires.

In the following, further exemplary embodiments of the ionization chamber will be explained. However, these embodiments also apply for the electrode for an ionization chamber and the method of producing an electrode.

According to another exemplary embodiment the ionization chamber further comprises a dielectric layer, wherein the dielectric layer is arranged in such a way that at least a portion of the plurality of nanowires is at least partially covered by the dielectric layer. In particular, the dielectric layer may be deposited as a continuous layer between the nanowires on the base member or substrate possibly leading to partially passivated nanowires. For example, each of the plurality of nanowires may comprise a base region attached to or connected to the base member and a tip region which may have a conical shape and the dielectric layer may be formed or deposited in such a way that the base region of at least some of the plurality of nanowires, or even of all of the plurality of nanowires, may be enclosed or covered by the dielectric layer, while the tip region may not be covered by the dielectric layer, i.e. is free from dielectric material.

According to another exemplary embodiment the ionization chamber further comprises a heating element.

The provision of a heating element may be suitable to aid decontamination of the ionization chamber, e.g. may aid the decontamination of a cavity of the detector. In particular, the provision of such a heating element may be useful in connection with cases in which an absorption or desorption of gases is involved when manufacturing and/or operating the ionization chamber.

Summarizing, according to an exemplary aspect of the invention an electrode for an ionization chamber or sensor may be provided which comprises a plurality of nanowires manufactured by processing, e.g. etching, a semiconductor substrate, e.g. a silicon substrate. The nanowires may have a tip region, which has a shape leading to a high electric field in the region about this tip, when a voltage is supplied to the nanowires. When integrated into a sensor, e.g. a gas sensor, the nanowires may be integrated onto a heating element to aid decontamination of the sensor. Thus, an ionization type gas sensor may be provided having a small size, low energy consumption and a high reliability. In particular, an ionization type sensor or ionization chamber may not suffer from difficulties in detecting gases having low adsorption energy or low electro negativity towards the active layer, which difficulties may arise when using gas-adsorptive type sensors.

An electrode or ionization type sensor using such an electrode according to an exemplary aspect of the invention may be used in a wide range of technical fields. For example, it may be used in the automotive field having a rapid growth in cabin air quality monitoring with large potential growth in emission control. It may also be used in the field of industrial safety, process control and emission monitoring. A further application may be in the medical field, e.g. field of breath and drugs, as in medical diagnosis for example. Another technical application may be environmental monitoring, e.g. monitoring of trace gases, for instance gases, which play an important role in urban pollution, including CO, $NO_x$, $CO_2$ and $H_2S$.

The exemplary embodiments and aspects defined above and further aspects of the invention are apparent from the example of embodiment to be described hereinafter and are explained with reference to the example of embodiment. It should be noted that features described in this application in connection with one exemplary embodiment or aspect of the invention may be combined with other exemplary embodiments or aspects.

BRIEF DESCRIPTION OF THE DRAWINGS

The invention will be described in more detail hereinafter with reference to examples of embodiment but to which the invention is not limited.

DESCRIPTION OF EMBODIMENTS

Figure 1:
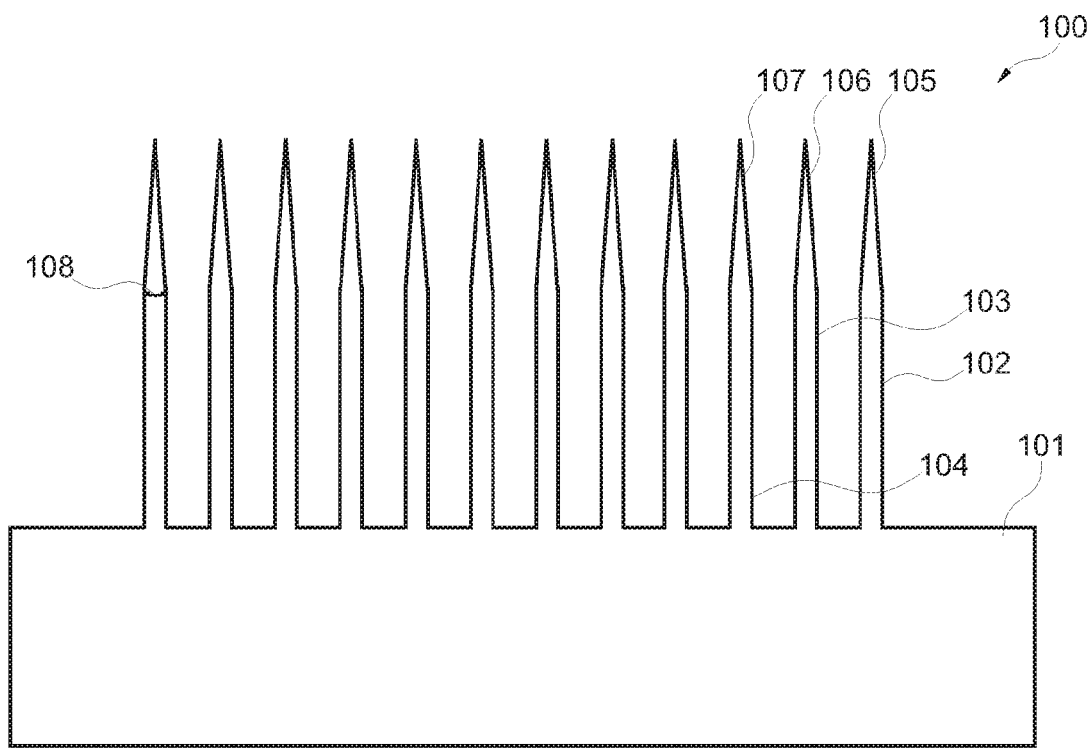
FIGS. 1 to 7 schematically show a procedure for manufacturing an ionization chamber according to an exemplary embodiment.

The illustration in the drawing is schematically. In different drawings, similar or identical elements are provided with similar or identical reference signs.

In the following, referring to FIGS. 1 to 7 exemplary steps of a process for manufacturing an ionization chamber according to an exemplary embodiment will be explained.

FIG. 1 shows a schematically substrate 100 comprising a base member 101 having arranged thereon a plurality of nanowires 102, 103, and 104. Etching a raw substrate e.g. a silicon substrate forms the nanowires. For the etching every known etching process may be used, e.g. etching processes that are used in CMOS processes.

The nanowires 102, 103, and 104 have comparable sharp tips 105, 106, and 107, respectively. For illustrative purposes, an angle 108 is indicated in FIG. 1, which angle 108 is twice the opening angle of the tips.

Figure 2:
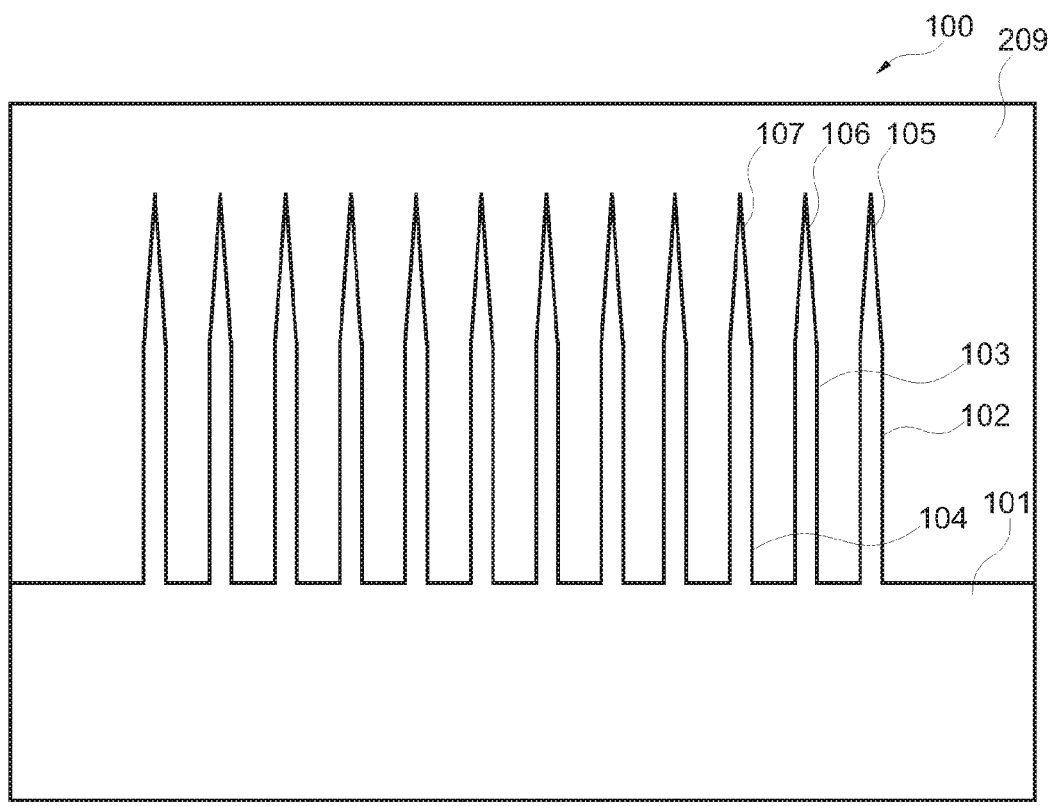

FIG. 2 shows the substrate 100 of FIG. 1 after a dielectric layer 209 has been formed over the substrate 100, in particular, on the base member 101 and around parts of the plurality of nanowires. The dielectric layer may be formed by known processes, e.g. by deposition, CVD or the like.

Figure 3:
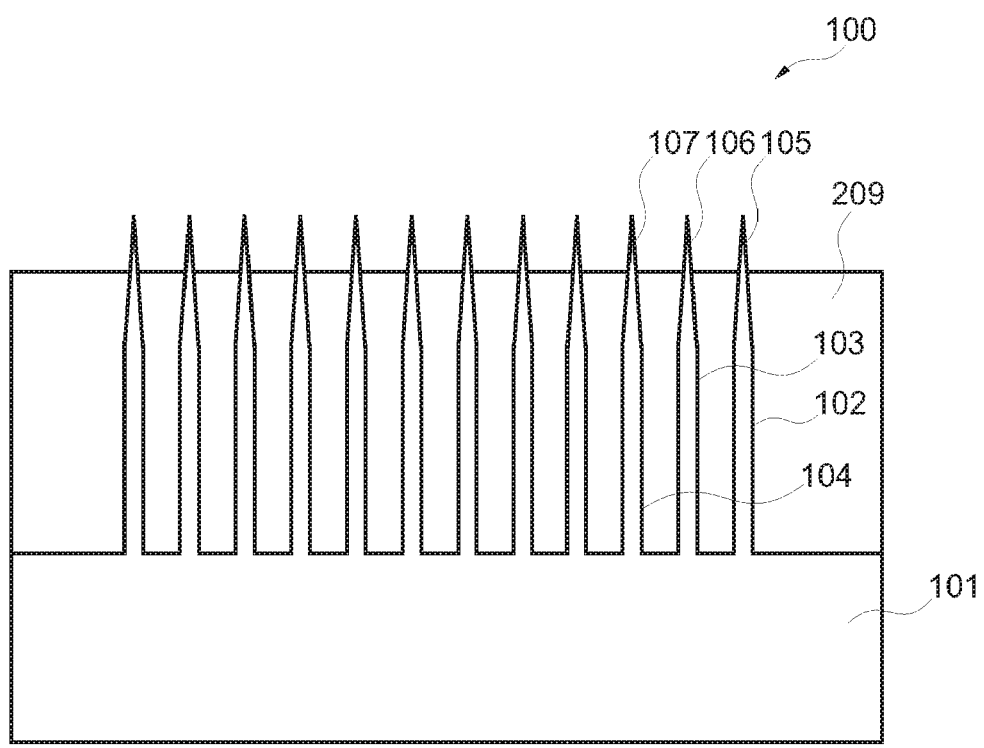

FIG. 3 shows the substrate 100 of FIG. 2 after the dielectric layer 209 has been planarized and/or partially removed so that the tip regions of the nanowires are exposed and not embedded by the dielectric layer any more.

Figure 4:
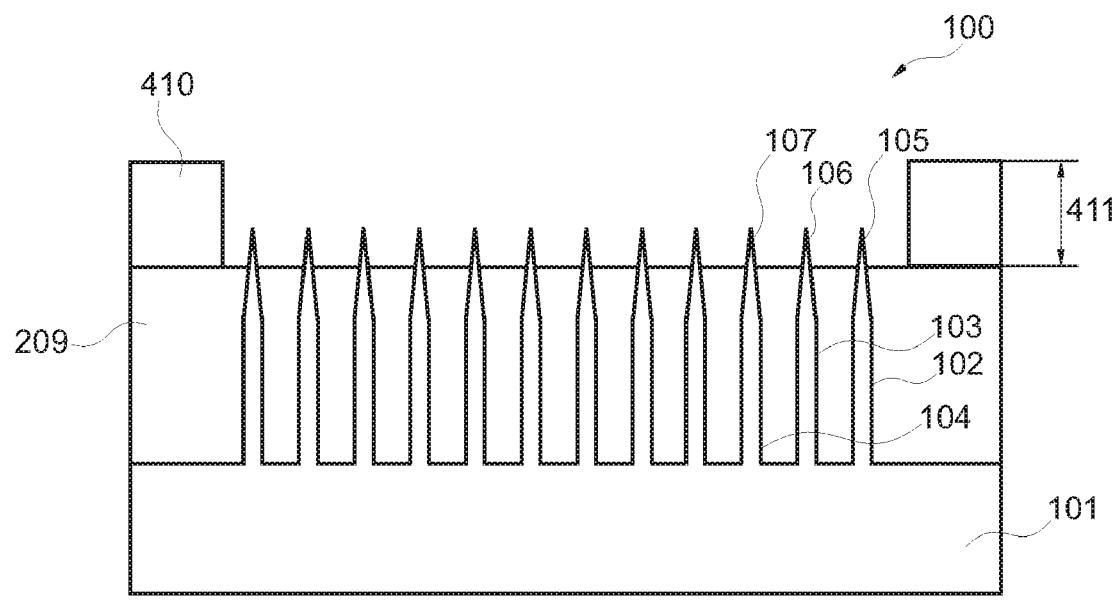

FIG. 4 shows the substrate 100 of FIG. 3 after a distance-defining layer 410, e.g. made of SiOC, has been deposited and structured or patterned. In particular, a thickness 411 of the SiOC layer may define a size of a gap between wire tips and a metal plate, e.g. a further electrode, of the ionization chamber.

Figure 5:
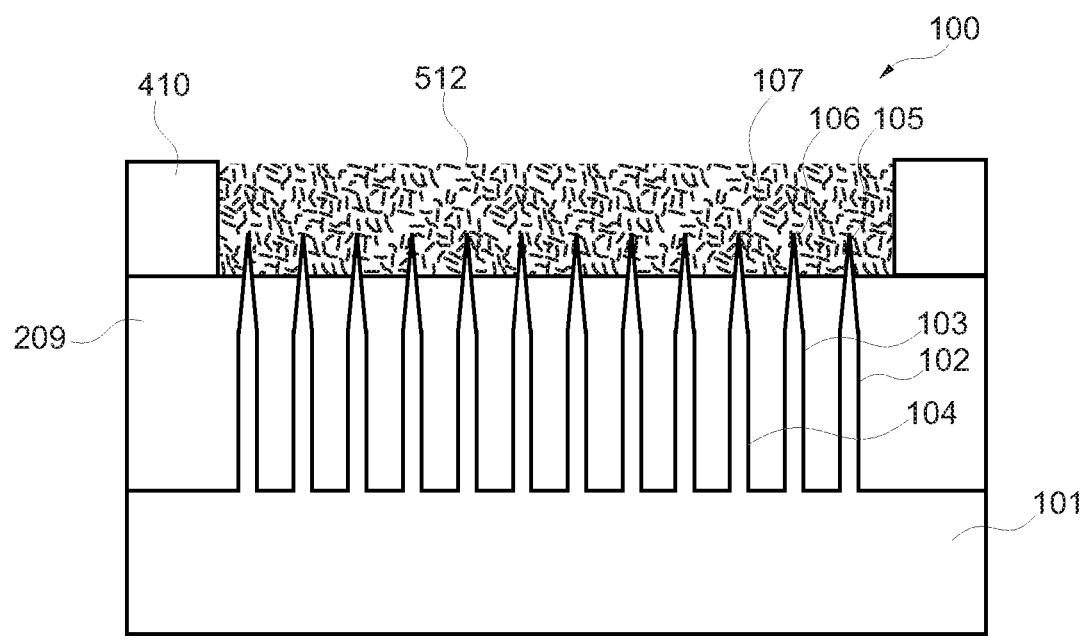

FIG. 5 shows the substrate 100 of FIG. 4 after deposition and planarization of a sacrifice layer 512. In particular, the sacrifice layer 512 may comprise or may be made of thermally degradable polymer (TDP) and may be formed on the tips of the nanowires. The SiOC layer 410 may form a stopping layer in the planaraization step.

Figure 6:
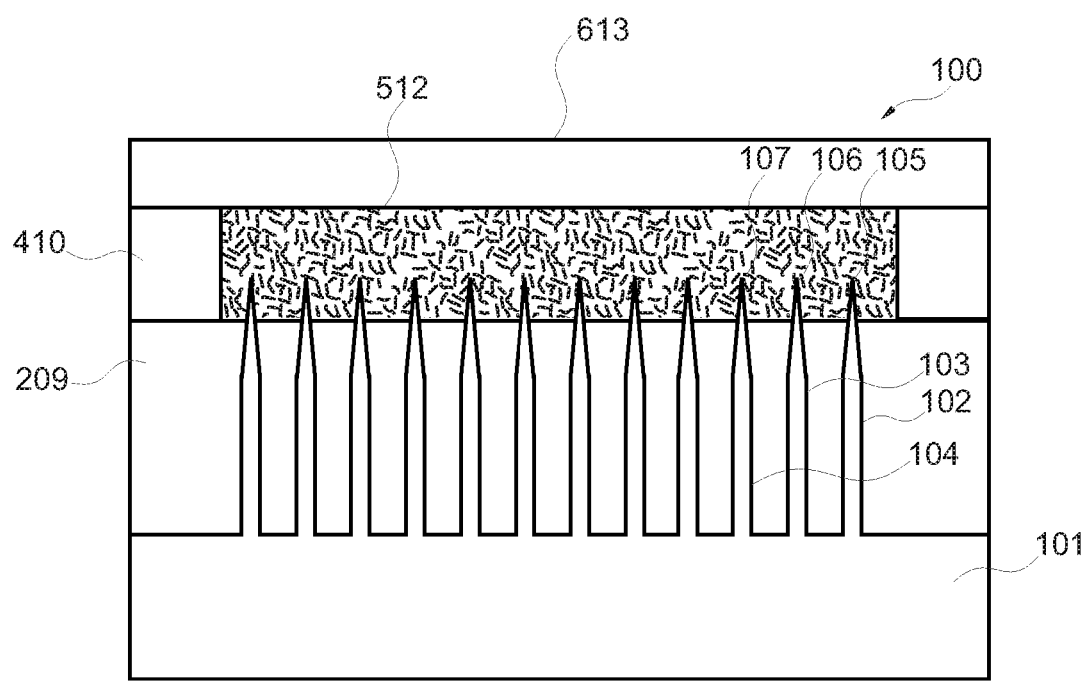

FIG. 6 shows the substrate 100 of FIG. 5 after a metal layer 613 has been formed on the planarized sacrifice layer 512 and the distance defining layer 410. The metal layer 613 may form a further or second electrode of the ionization chamber.

Figure 7:
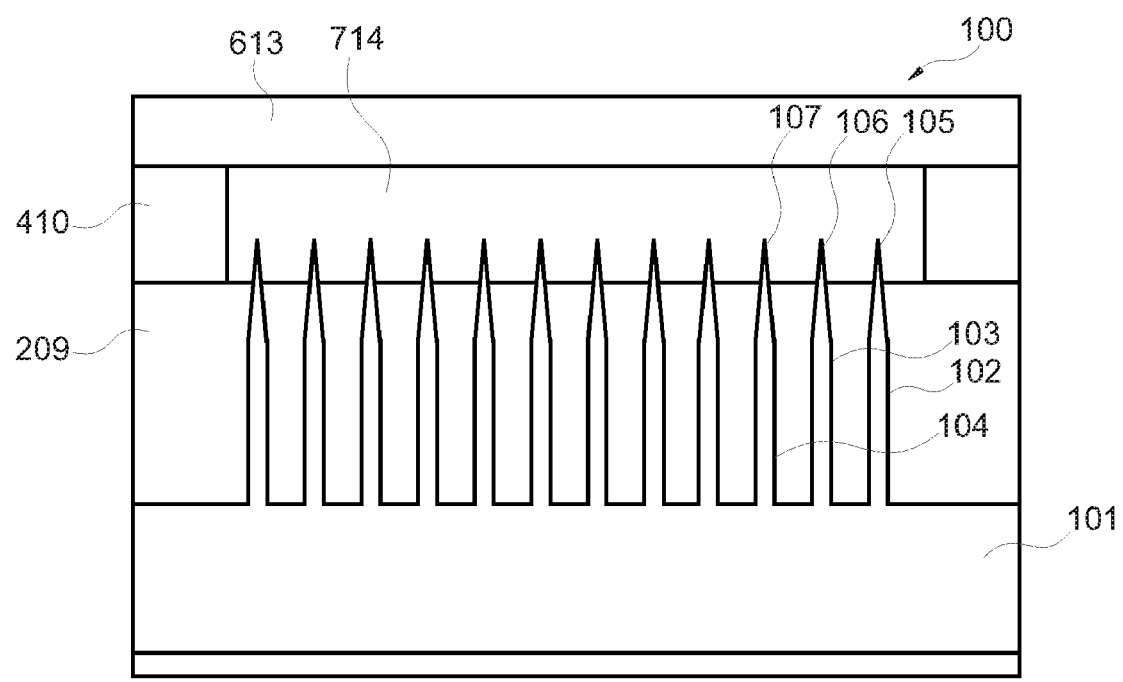

FIG. 7 shows the substrate 100 of FIG. 6 after the sacrifice layer 512 has been removed so that a cavity 714 is build forming a chamber of the ionization chamber. In case a TDP layer is used for the sacrifice layer 512, the TDA layer may be removed by decomposition of the same. By removing the sacrifice layer 512 the tips of the nanowires are exposed again and extend into the formed cavity 714.

Figure 8:
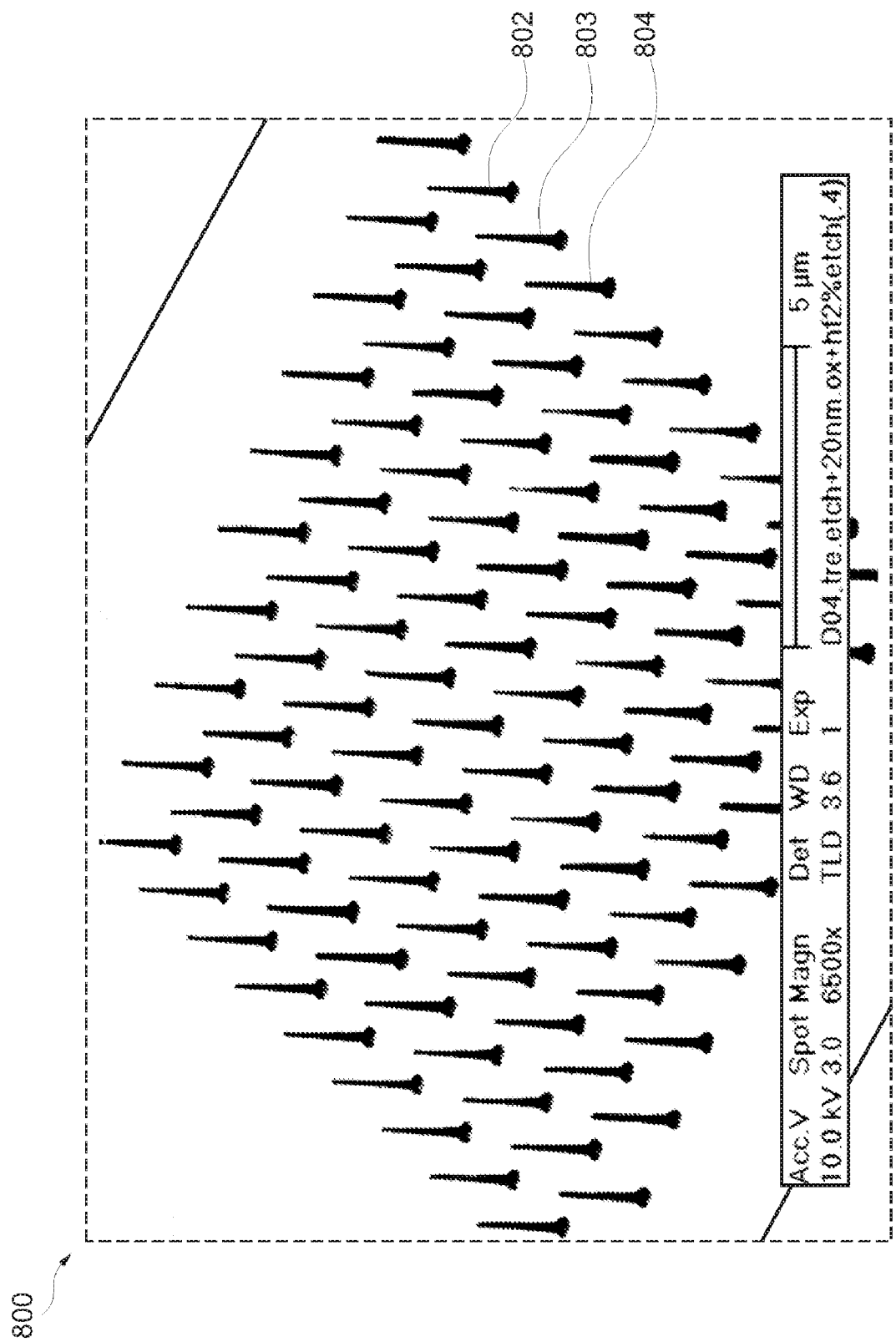
FIG. 8 shows a microscopic image of an electrode according to an exemplary embodiment.

FIG. 8 shows a microscopic image of an electrode 800 according to an exemplary embodiment. In particular, FIG. 8 shows an array of a plurality of nanowires 802, 803, and 804 arranged in a regular pattern on a substrate. In FIG. 8 the pattern is a regular rectangular or square pattern so that the individual nanowires have an equal spacing to the closest neighbors. As can be seen from the legend the spacing is in the order of 1 μm and the height or length of the nanowires is in the range of 1 μm as well.

Figure 9:
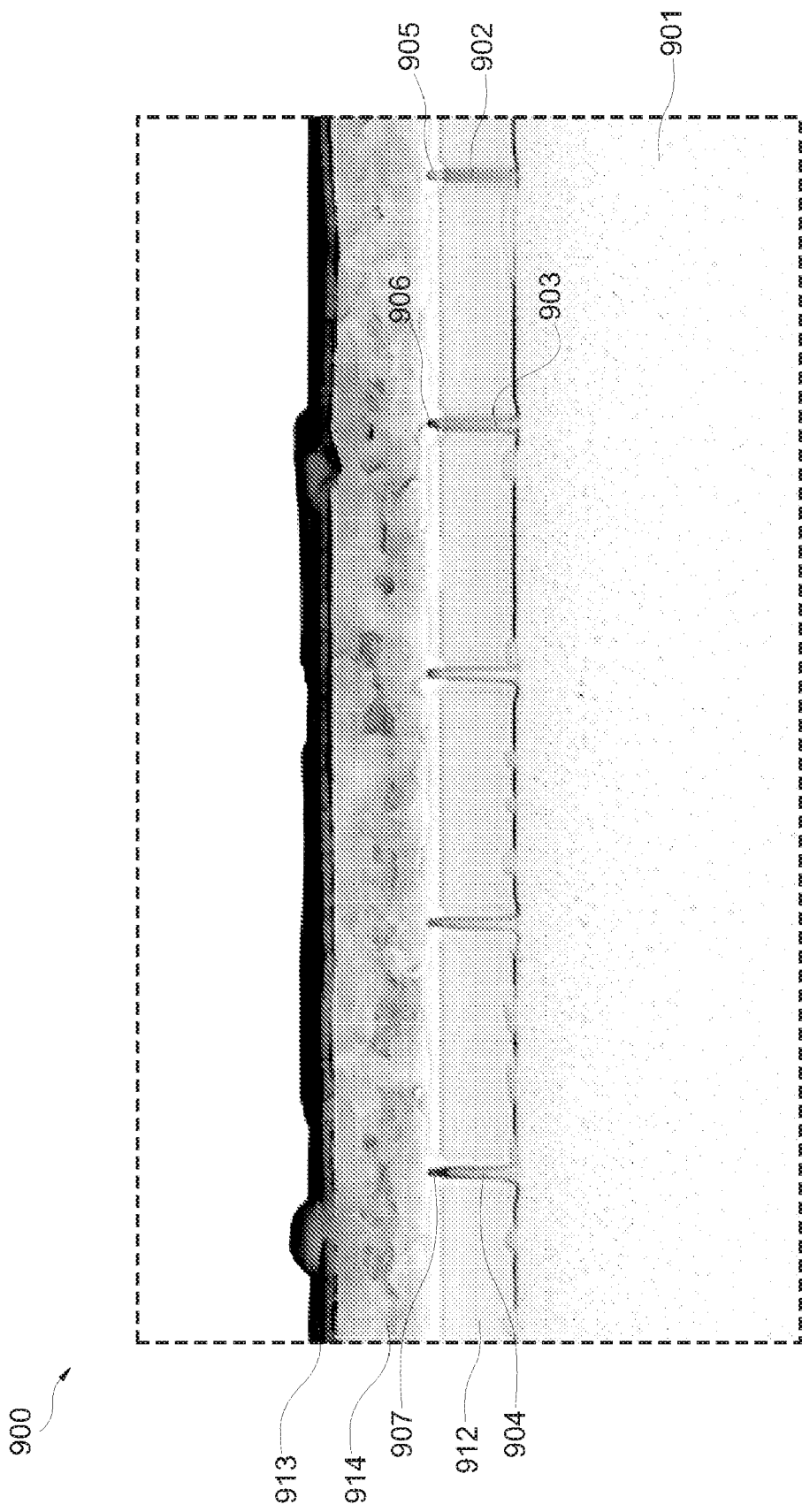
FIG. 9 shows a microscopic image of an ionization chamber according to an exemplary embodiment.

FIG. 9 shows a microscopic image of an ionization chamber according to an exemplary embodiment. In particular, FIG. 9 shows a cross-sectional image of an ionization chamber 900. The ionization chamber 900 comprises a substrate 901 having a plurality of nanowires 902, 903, and 904 extending therefrom. On the substrate 901 and between the nanowires a dielectric layer 909 is formed in such a way that tips 905, 906, and 907 of the nanowires 902, 903, and 904 are not embedded by the dielectric layer 912 but extend into a cavity 914 of the ionization chamber 900. Furthermore, a metal plate or second electrode 913 can be seen in FIG. 9. When operating the ionization chamber 900 a voltage supply may be coupled to the nanowires generating a high electric field in the region of the free tips which is high enough to breakdown fluids, e.g. gases, passing through the cavity 914

It should be noted that the term "comprising" does not exclude other elements or features and the "a" or "an" does not exclude a plurality. Also elements described in association with different embodiments or aspects may be combined. It should also be noted that reference signs in the claims shall not be construed as limiting the scope of the claims.

The invention claimed is:

1. An ionization chamber for sensing molecule particles, the ionization chamber comprising:
   an electrode including a substrate having a first material, and a plurality of integral nanowires extending from the substrate and manufactured from the first material of the substrate;
   a cavity through which fluids can pass; and
   a further electrode facing the electrode,
   wherein at least some of the plurality of nanowires comprise a tip region extending into the cavity; and
   wherein the further electrode is arranged in such a way that the tip region and the electrode are facing each other.

2. The ionization chamber according to claim 1, wherein the plurality of nanowires is manufactured by etching.

3. The ionization chamber according to claim 1, wherein the first material is a semiconductor material.

4. The ionization chamber according to claim 1, wherein at least some of the nanowires are at least partially silicided.

5. The ionization chamber according to claim 1, further comprising:
   a dielectric layer,
   wherein the dielectric layer is arranged in such a way that at least a portion of the plurality of nanowires is at least partially covered by the dielectric layer.

6. The ionization chamber according to claim 1, further comprising:
   a heating element.

7. The ionization chamber according to claim 1, wherein the longitudinal size of the nanowires is between 50 nm and 20 μm.

8. The ionization chamber according to claim 1, wherein the diameter of the nanowires is between 2-200 nm.

9. The ionization chamber according to claim 1, wherein the longitudinal size of the nanowires is between 100 nm and 10 μm, and the diameter of the nanowires is between 5-100 nm.

10. The ionization chamber according to claim 1, wherein the tip regions each have an opening angle that is between 10° to 25°.

11. The ionization chamber according to claim 1, wherein the tip regions each have an opening angle that is between 5° to 10°.

12. A method of manufacturing an ionization chamber, the method comprising:
provided a substrate,
patterning the substrate in such a way that a plurality of integral nanowires is generated which extend from the substrate by selective removal processing of the substrate, at least some of the nanowires comprising a tip region;
depositing and patterning a distance defining layer for defining a distance between the tip regions of the at least some of the plurality of nanowires and a further electrode to be formed;
depositing and planarizing a sacrificial layer over the tip regions of the at least some of the plurality of nanowires using the patterned distance defining layer as a stop layer in said planarization step;
forming the further electrode on the planarized sacrificial layer and the patterned distance defining layer; and
removing the sacrificial layer such that the tip regions of the at least some of the plurality of nanowires are exposed again and a cavity through which fluids can pass is formed.

13. The method according to claim 12, wherein the substrate comprises silicon.

14. The method according to claim 12, wherein the patterning of the substrate is performed by etching.

15. The method according to claim 12, further comprising:
forming a dielectric layer onto the substrate in such a way that at least some of the plurality of nanowires are covered partially by the dielectric layer, wherein said tip regions are free of the dielectric layer.

16. The method according to claim 12, wherein the longitudinal size of the nanowires is between 50 nm and 20 μm.

17. The method according to claim 12, wherein the diameter of the nanowires is between 2-200 nm.

18. The method according to claim 12, wherein the longitudinal size of the nanowires is between 100 nm and 10 μm, and the diameter of the nanowires is between 5-100 nm.

19. The method according to claim 12, wherein the tip regions each have an opening angle that is between 10° to 25°.

20. The method according to claim 12, wherein the tip regions each have an opening angle that is between 5° to 10°.

* * * * *